US008796218B2

(12) United States Patent
Svanborg et al.

(10) Patent No.: US 8,796,218 B2
(45) Date of Patent: Aug. 5, 2014

(54) COMPLEX AND PRODUCTION PROCESS

(75) Inventors: Catharina Svanborg, Lund (SE);
Kenneth Hun Mok, Dublin (IE);
Ann-Kristin Mossberg, Loddekopinge (SE); Jenny Petterson-Kastberg, Lund (SE)

(73) Assignee: Hamlet Pharma AB (SE)

( * ) Notice: Subject to any disclaimer, the term of this patent is extended or adjusted under 35 U.S.C. 154(b) by 365 days.

(21) Appl. No.: 13/143,785

(22) PCT Filed: Jan. 8, 2010

(86) PCT No.: PCT/GB2010/050024
§ 371 (c)(1),
(2), (4) Date: Oct. 14, 2011

(87) PCT Pub. No.: WO2010/079362
PCT Pub. Date: Jul. 15, 2010

(65) Prior Publication Data
US 2012/0028883 A1 Feb. 2, 2012

(30) Foreign Application Priority Data

Jan. 9, 2009 (GB) .................................. 0900260.1
Apr. 9, 2009 (GB) .................................. 0906199.5

(51) Int. Cl.
*A61K 38/00* (2006.01)
*A61P 35/00* (2006.01)
(52) U.S. Cl.
USPC .......................................................... 514/19.3
(58) Field of Classification Search
None
See application file for complete search history.

(56) References Cited

U.S. PATENT DOCUMENTS

2003/0055105 A1   3/2003   Ito et al.

FOREIGN PATENT DOCUMENTS

| WO | 99/26979 A1 | 6/1999 |
| WO | 99/27967 A1 | 6/1999 |
| WO | 01/17524 A1 | 3/2001 |
| WO | 03/074547 A2 | 9/2003 |
| WO | 2008058547 A2 | 5/2008 |
| WO | 2008138348 A1 | 11/2008 |
| WO | 2010/079362 A1 | 7/2010 |
| WO | 2010/131237 A1 | 11/2010 |
| WO | 2012/069836 A2 | 5/2012 |

OTHER PUBLICATIONS

Fast et al., "Stability of HAMLET—A kinetically trapped alpha-lacralbumin oleic acid complex", Protein Science, 2005, pp. 329-340, vol. 14.
Mok et al., "HAMLET, protein folding, and tumor cell death", Biochemical and Biophysical Research Communications, 2007, pp. 1-7, vol. 354.
Svensson et al., "Conversion of alpha-lactalbumin to a protein inducing apoptosis", Proceedings of the National Academy of Science, 2000, pp. 4221-4226, vol. 97, No. 8.
Written Opinion and International Search Report for PCT/GB2010/050024 dated Mar. 23, 2010, 13 pages.
Anderson et al., "Functional identification of calcium binding residues in bovine alpha-lactalbumin", Biochemistry, 1997, pp. 11648-11654, vol. 36, No. 39.
Mossberg et al., Bladder cancers respond to intravesical instillation of HAMLET (human alpha-lactalbumin made lethal to tumor cells), International Journal of Cancer, 2007, pp. 1352-1359, vol. 121.
Peng et al., "Local structural preferences in the alpha-lactalbumin molten globule", Biochemistry, 1995, pp. 3248-3252, vol. 34, No. 10.
Schulman et al., "Different subdomains are most protected from hydrogen exchange in the molten globule and native states of human alpha-lactalbumin", Journal of Molecular Biology, 1995, pp. 651-657, vol. 253, No. 5.
Pettersson et al., "alpha-Lactalbumin species variation, HAMLET formation, and tumor cell death", Biochemistry Biophysics Research Communications, 2006, pp. 260-270, vol. 345, No. 1.
Svensson et al., "Molecular Characterization of alpha-Lactalbumin Folding Variants That Induce Apoptosis in Tumor Cells", The Journal of Biological Chemistry, 1999, pp. 6388-6396, vol. 274, No. 10.
Abbott et al., "Microbial Transformation of A23187, a Divalent Cation Ionophore Antibiotic", Antimicrobial Agents and Chemotherapy, 1979, pp. 808-812, vol. 16, No. 6.
Abramoff et al., "Image Processing with ImageJ", Biophotonics International, Jul. 2004, 7 pgs.
Aits et al., "HAMLET (human α-lactalbumin made lethal to tumor cells) triggers autophagic tumor cell death", Int. J. Cancer, 2009, pp. 1008-1019, vol. 124.
Arcangeli et al., "Targeting Ion Channels in Cancer: A Novel Frontier in Antineoplastic Therapy", Current Medicinal Chemistry, 2009, pp. 66-93, vol. 16, No. 1.
Chua et al., "A novel normalization method for effective removal of systematic variation in microarray data", Nucleic Acids Research, 2006, pp. e38, 7 pgs., vol. 34, No. 5.
Cobb, "MAP kinase pathways", Progress in Biophysics & Molecular Biology, 1999, pp. 479-500, vol. 71.
Correa-Meyer et al., "Cyclic stretch activates ERK1/2 via G proteins and EGFR in alveolar epithelial cells", Am. J. Physiol. Lung Cell Mol. Physiol., 2002, pp. L883-L891, vol. 282.

(Continued)

*Primary Examiner* — Thomas Heard

(57) ABSTRACT

A method for preparing a biologically active complex, said method comprising a recombinant protein having the sequence of α-lactalbumin, such as human α-lactalbumin or a fragment thereof but which lacks intra-molecular disulfide bonds, and oleic acid, and process for preparing this are described and claimed. The recombinant protein suitably has cysteines found in the native protein changed to other amino acids, such as alanine. Improvements in recombinant expression, process rationalisation and yields of biologically active complexes, as well as the complexes obtained are also described and claimed.

16 Claims, 7 Drawing Sheets

(56) References Cited

OTHER PUBLICATIONS

Figure 1:
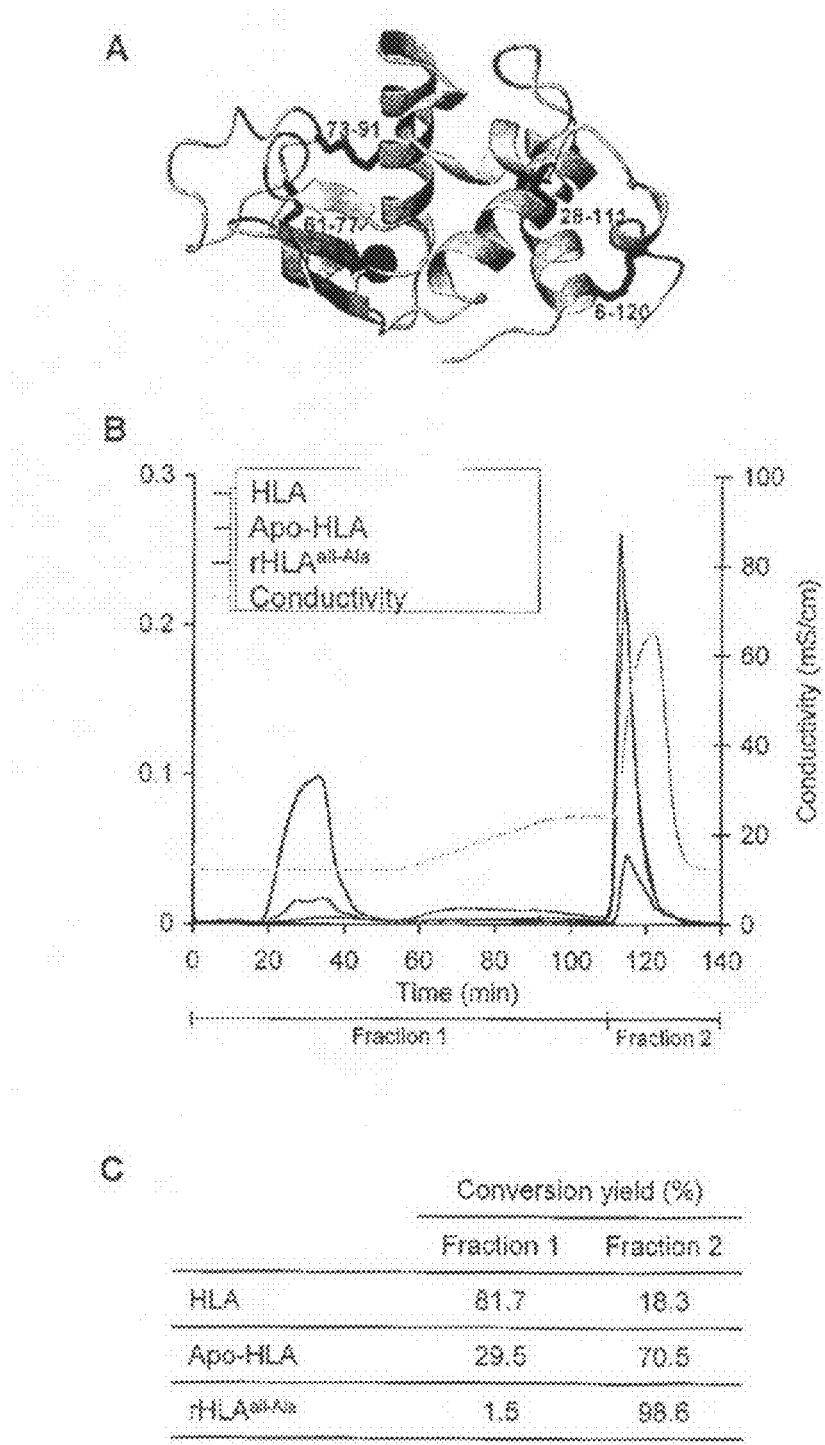

Cuenda et al., "p38 MAP-Kinases pathway regulation, function and role in human diseases", Biochimica et Biophysica Acta, 2007, pp. 1358-1375, vol. 1773.

Dennis et al., "DAVID: Database for Annotation, Visualization, and Integrated Discovery", Genome Biology, 2003, p. 3, 19 pgs., vol. 4, No. 5.

Fabian et al., "A small molecule-kinase interaction map for clinical kinase inhibitors", Nature Biotechnology, 2005, pp. 329-336, vol. 23, No. 3.

Fischer et al., "Human α-Lactalbumin Made Lethal to Tumor Cells (HAMLET) Kills Human Glioblastoma Cells in Brain Xenografts by an Apoptosis-Like Mechanism and Prolongs Survival", Cancer Research, 2004, pp. 2105-2112, vol. 64.

GB Search Report from related Application No. GB1019937.0, dated Mar. 24, 2011, 5 pgs.

Gustafsson et al., "Treatment of Skin Papillomas with Topical α-Lactalbumin-Oleic Acid", The New England Journal of Medicine, 2004, pp. 2663-2672, vol. 350, No. 26.

Hakansson et al., "Apoptosis induced by a human milk protein", PNAS, 1995, pp. 8064-8068, vol. 92.

Huang et al., "Cell tension, matrix mechanics, and cancer development", Cancer Cell, 2005, pp. 175-176, vol. 8.

Huff et al., "Pathological and functional amyloid formation orchestrated by the secretory pathway", Current Opinion in Structural Biology, 2003, pp. 674-682, vol. 13.

International Search Report and Written Opinion from related application, PCT/GB2011/052310, dated Jun. 26, 2012, 13 pgs.

Irizarry et al., "Exploration, normalization, and summaries of high density oligonucleotide array probe level data", Biostatistics, 2003, pp. 249-264, vol. 4, No. 2.

Karpman et al., "Apoptosis of Renal Cortical Cells in the Hemolytic-Uremic Syndrome: In Vivo and In Vitro Studies", Infection and Immunity, 1998, pp. 636-644, vol. 66, No. 2.

Kuwajima, "The molten globule state of α-lactalbumin", FASEB J., 1996, pp. 102-109, vol. 1.

Mossberg et al., "HAMLET Treatment Delays Bladder Cancer Development", The Journal of Urology, 2010, pp. 1590-1597, vol. 183.

Owens et al., "Differential regulation of MAP kinase signalling by dual-specificity protein phosphatases", Oncogene, 2007, pp. 3203-3213, vol. 26.

Pfeil, "Is thermally denatured protein unfolded? The example of α-lactalbumin", Biochimica et Biophysica Acta, 1987, pp. 114-116, vol. 911.

Rammer et al., "BAMLET Activates a Lysosomal Cell Death Program in Cancer Cells", Molecular Cancer Therapeutics, 2010, vol. 9, No. 1, Abstract Only.

Svanborg et al., "HAMLET Kills Tumor Cells by an Apoptosis-Like Mechanism—Cellular, Molecular, and Therapeutic Aspects", Advances in Cancer Research, 2003, pp. 1-29, vol. 88.

Vukojevic et al., "Lipoprotein Complex of Equine Lysozyme with Oleic Acid (ELOA) Interactions with the Plasma Membrane of Live Cells", Langmuir, 2010, pp. 14782-14787, vol. 26, No. 18.

Wang et al., "Stress-Induced Phosphorylation and Activation of the Transcription Factor CHOP (GADD153) by p38 MAP Kinase", Science, 1996, pp. 1347-1349, vol. 272, No. 5266.

Wolf et al., "Multi-step pericellular proteolysis controls the transition from individual to collective cancer cell invasion", Nature Cell Biology, 2007, pp. 893-904, vol. 9, and Supplementary Information.

Xia et al., "Opposing Effects of ERK and JNK-p38 MAP Kinases on Apoptosis", Science, 1995, pp. 1326-1331, vol. 270, No. 5240.

Yoshida et al., "XBP1 mRNA Is Induced by ATF6 and Spliced by IRE1 in Response to ER Stress to Produce a Highly Active Transcription Factor", Cell, 2001, pp. 881-891, vol. 107.

Figure 2
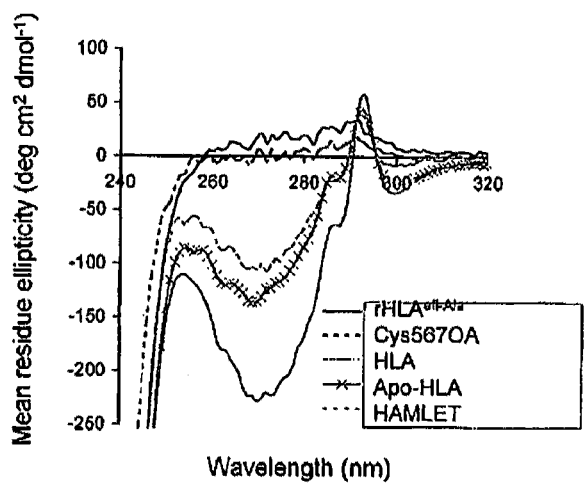
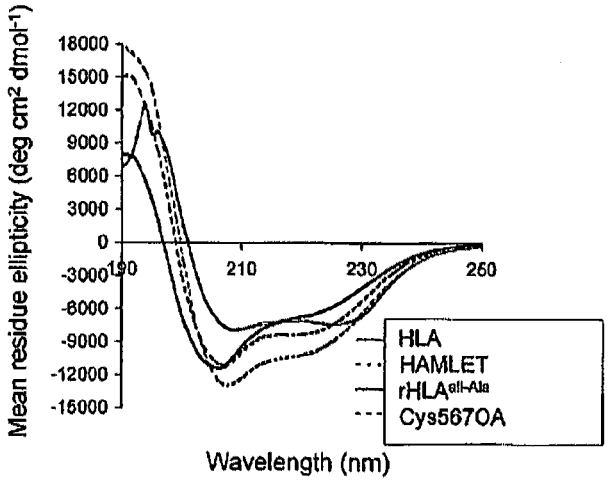

Figure 3
A
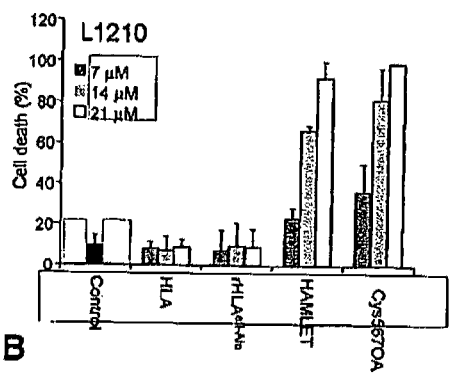 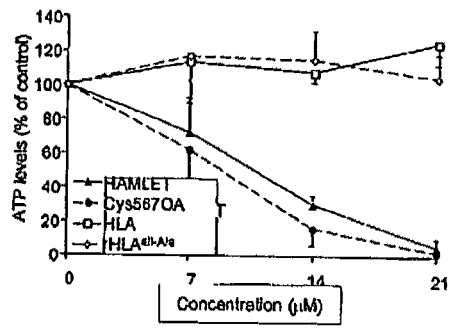
B
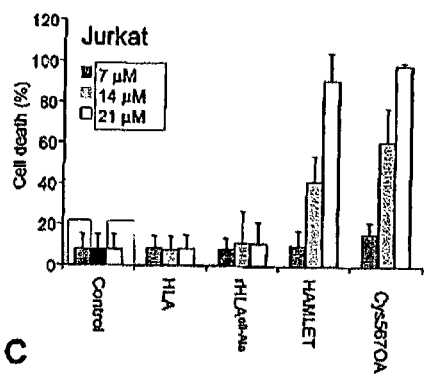 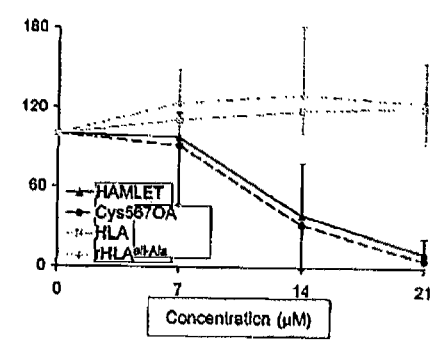
C
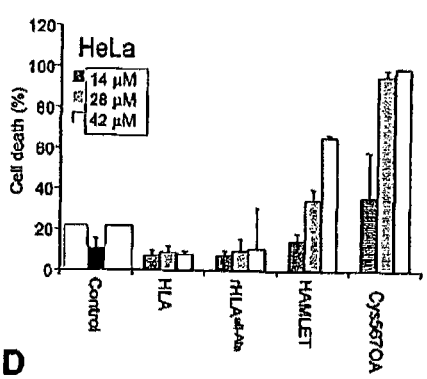 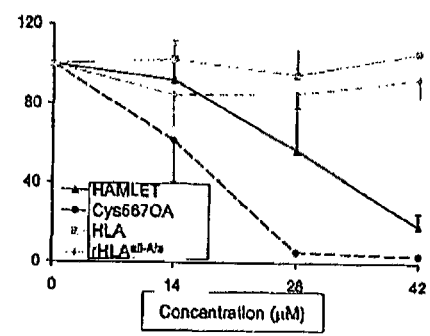
D
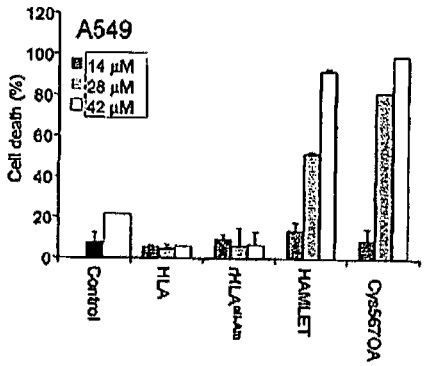 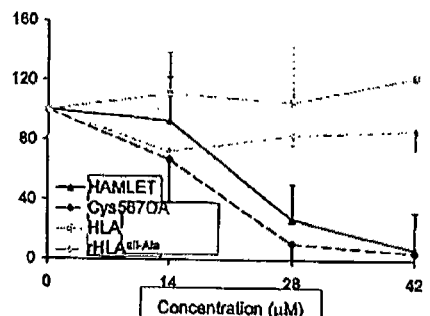

COMPLEX AND PRODUCTION PROCESS

The present invention relates to a process for the preparation of a therapeutic protein complex, and to apparatus and reagents for use in the process.

Mutated forms of recombinant α-lactalbumin are known in the art, and although many of the properties found for the folded and molten globular forms have been shown to be similar to the native protein, it is generally accepted that there is generally a reduction in stability in the mutated forms. α-Lactalbumin itself in a partially unfolded or molten globule state has been used previously to form biologically active complexes, (Svensson et al. Proc. Natl. Acad. Sci. USA (2000) 97(8) 4221-4226).

However, the applicants have found that a particular type of recombinant protein, can be used to produce therapeutically active complexes with unique compositional features and structures, as demonstrated by n.m.r. The complexes retain useful biological and activity in spite of these differences and furthermore can be prepared efficiently.

Thus according to the present invention there is provided a method of producing a biologically active complex, said method comprising contacting a recombinant protein having the sequence of α-lactalbumin or a fragment thereof but which lacks intra-molecular disulfide bonds or cross-links, with oleic acid under conditions in which a biologically active complex is formed and isolating the complex.

By ensuring that the recombinant protein lacks intra-molecular disulfide crosslinks, the molecule will be three-dimensionally non-native and completely inactive in terms of its original endogenous biological activity. This may be achieved for example by changing cysteine residues in the native α-lactalbumin to other residues, in particular alanine residues, although other means, for example by adding thiol compounds, or altering the pH of the protein may be considered. Preferably all cysteine residues will be changed to other residues, such as alanine residues.

The expression "biologically active" as used herein means that the complex is able to induce tumour cell death, in particular by apoptosis in tumour cells and/or has a bactericidal effect not seen with the native monomeric α-lactalbumin forms.

The term "fragment thereof" refers to any portion of the given amino acid sequence which will form a complex with the similar activity to complexes including the complete α-lactalbumin amino acid sequence. Fragments may comprise more than one portion from within the full-length protein, joined together. Portions will suitably comprise at least 5 and preferably at least 10 consecutive amino acids from the basic sequence.

Suitable fragments will be deletion mutants comprising at least 20 amino acids, and more preferably at least 100 amino acids in length. They include small regions from the protein or combinations of these.

Suitable fragments will include the region which forms the interface between the alpha and beta domains is, in human α-lactalbumin, defined by amino acids 34-38 and 82-86 in the structure. Thus suitable fragments will include these regions, and preferably the entire region from amino acid 34-86 of the native protein. However, other active fragments may be found.

In particular the recombinant protein is based upon the sequence of human α-lactalbumin but α-lactalbumin from other sources, including bovine or ovine α-lactalbumin may be used to derive the recombinant protein.

Methods that may be used to convert recombinant protein and oleic acid to biologically active complex are analogous to those described for example in WO99/26979 and WO2008/138348, the content of which is incorporated herein by reference. However, in accordance with the method of the invention, a distinct biologically active product is more readily obtainable in good yield.

In particular, when using the method of the invention, high yields of biologically active complex are obtained conveniently, in particular from a single fraction eluting from a column and without the need for a prolonged folding process.

The recombinant protein as defined above is suitably contacted with the oleic acid under conditions which allow ion exchange to take place in particular on an ion exchange column, specifically an anion exchange column such as a DEAE-Trisacryl M column (available from BioSepra, Ville-neuf, France). The column is suitably "pre-conditioned" with oleic acid before the recombinant protein is applied to it. This may be achieved by eluting or conditioning the column first with oleic acid. Suitably the oleic acid is eluted through a column containing new unused ion exchange material such as DEAE Trisacryl. Suitable elution buffers include Tris-HCl with a pH of 8.5. The amount of oleic acid composition applied to the column in this way may be small depending upon factors such as the size of the column and the volume of recombinant protein required to be converted to biologically active complex. For example, it has been found that only 10 mg of oleic acid can be used to condition a column of 14 cm×1.6 cm.

After the recombinant protein has been applied to the column (for example in solution in a suitable buffer), it is then eluted with a linear salt gradient, and the fraction eluting at high salt (1M NaCl or equivalent) is isolated. Using the method of the invention, substantially all the product is obtainable from this one peak, whereas previously, two peaks have always been required to be isolated.

This provides a significant enhancement of production efficiency and purity of product since there is no need to fold the expressed protein to the native state and no need to obtain and pool multiple fractions.

Thus in a particular embodiment, the invention provides a method of producing a biologically active complex, said method comprising contacting a recombinant protein having the sequence of α-lactalbumin or a fragment thereof but which lacks intra-molecular disulfide bonds (crosslinks), with oleic acid on an anion exchange column under conditions in which a biologically active complex is formed, eluting the column with a salt gradient and isolating the complex from a single fraction eluting at high salt concentration.

The expression "high salt concentration" refers to concentrations of salts with cations such as halides and in particular chlorides at concentrations in excess of 0.5M, for example in excess of 0.75M and in particular at about 1M. The concentration required may vary depending upon the salt used, but in a particular embodiment, the salt is NaCl, and suitably 1M NaCl.

In accordance with the invention, the "recombinant protein having the sequence of α-lactalbumin" comprises a protein having the sequence of native mature α-lactalbumin but which has all of the cysteines found at positions 6, 28, 61, 73, 77, 91, 111 and 120 in the full length sequence of mature human α-lactalbumin mutated to other amino acids, such as alanine, which do not give rise to disulphide bridges. Thus a particular of a protein that may be utilised in accordance with the invention comprises a protein of SEQ ID NO 1.

```
                                                   (SEQ ID NO 1)
KQFTKAELSQLLKDIDGYGGIALPELIATMFHTSGYDTQAIVENNESTEY

GLFQISNKLWAKSSQVPQSRNIADISADKFLDDDITDDIMAAKKILDIKG

IDYWLAHKALATEKLEQWLAEKL
``` where the bold type indicates positions of mutations of cysteines in native human α-lactalbumin.

The applicants have found that some amino acid residues, for example up to 20 amino acids, may be attached at the terminal ends of the protein, if convenient, for example for expression purposes. Thus in particular, a recombinant protein as shown in SEQ ID NO. 1 but with an additional methionine at the N-terminus (SEQ ID NO 2 shown below) has been used in the method of the invention. The complex obtained using this sequence has been designated Cys567OA. This complex shows unique properties when examined by n.m.r. and thus it forms a particular aspect of the invention.

The recombinant protein used in the method is suitably produced in pure form, using conventional recombinant expression methods. In particular, DNA encoding the required recombinant α-lactalbumin can be inserted into suitable expression vectors such as plasmids, which can then be employed to transform host cells, for example, prokaryotic cells such as E. coli or eukaryotic cells such as particular insect cells using conventional methods.

By using the recombinant protein as described above, there is no need for pretreatment steps, for example by treatment with a calcium chelating agent such as EDTA (ethylene diamine tetraacetic acid), subjecting the material to low pH or high temperature, in order to remove calcium and increase the amount of molten globule-like material present. Such a step is generally preferable when using native human α-lactalbumin or modified forms in which some cysteine residues remain in order to generate a biologically active complex.

Suitably the oleic acid used in the process is in pure form although a casein containing fraction of human milk can provide a convenient source of this material and may be used in the process as has been demonstrated previously.

A pre-treated column can be used repeatedly to convert numerous fractions of a recombinant protein having the sequence of α-lactalbumin or a fragment thereof to biologically active complex as described above. Once the column is exhausted or the conversion rate drops to unacceptable levels, the pre-treatment step can be repeated in order to restore the complex production activity.

The product obtained using the process of the invention is novel and therefore forms a further aspect of the invention.

Thus, the invention further provides a biologically active complex of a recombinant protein having the sequence of α-lactalbumin or a fragment thereof as described above, and oleic acid. In particular the invention provides a biologically active complex comprising a recombinant protein of SEQ ID NO 2 and oleic acid, that has been designated Cys567OA.

```
                                                   (SEQ ID NO 2)
MKQFTKAELSQLLKDIDGYGGIALPELIATMFHTSGYDTQAIVENNEST

EYGLFQISNKLWAKSSQVPQSRNIADISADKFLDDDITDDIMAAKKILD

IKGIDYWLAHKALATEKLEQWLAEKL
```

The complex has been found to be biologically active in that it has activity in inducing tumour cell-death for instance by apoptosis and/or have a bactericidal effect that is at least equal to that obtained with other biologically active complexes such as HAMLET.

Thus, it may be formulated into useful pharmaceutical compositions by combining it with pharmaceutically acceptable carriers in the conventional manner. Such compositions form a further aspect of the invention.

The compositions in accordance with this aspect of invention are suitably pharmaceutical compositions in a form suitable for topical use, for example as creams, ointments, gels, or aqueous or oily solutions or suspensions. These may include the commonly known carriers, fillers and/or expedients, which are pharmaceutically acceptable.

Topical solutions or creams suitably contain an emulsifying agent for the protein complex together with a diluent or cream base.

The daily dose of the complex varies and is dependant on the patient, the nature of the condition being treated etc. in accordance with normal clinical practice. As a general rule from 2 to 200 mg/dose of the biologically active complex is used for each administration.

In a further aspect of the invention, there is provided a method for treating cancer which comprises administering to a patient in need thereof, a biologically active complex as described above.

In particular, the complex may be used to treat cancers such as human skin papillomas, human bladder cancer and glioblastomas. In the latter case, administration may be by infusion as is known in the art.

The invention further provides the biologically active complex as defined above for use in therapy, in particular in the treatment of cancer.

That the elimination of cysteine residues would lead to an enhanced yield of biologically active complex is unexpected.

Thus, yet a further aspect of the invention provides a method for increasing the yield of a biologically active complex obtainable by a process comprising contacting α-lactalbumin or a fragment thereof and oleic acid under ion exchange conditions, said method comprising using a recombinant protein having the sequence of α-lactalbumin or a fragment thereof but which lacks at least some of the intramolecular disulfide crosslinks found in the native protein in said process.

As before, the disulfide cross-links are suitably eliminated by changing cysteine residues to other amino acids. In particular, all disulfide crosslinks are eliminated, for example by changing all cysteine residues to different amino acids, for instance alanine.

Furthermore, the invention provides the use of a recombinant protein having the sequence of having the sequence of α-lactalbumin or a fragment thereof but which lacks intramolecular disulfide bonds or crosslinks, in the preparation of biologically active complexes. In particular, the recombinant protein has the sequence of human α-lactalbumin or a fragment thereof in which cysteine residues and in particular all cysteine residues are changed to different amino acids.

Recombinant proteins used in these aspects of the invention may contain additional amino acids as described above.

The invention will now be particularly described by way of example with reference to the accompanying diagrammatic drawings in which:

FIG. 1 relates to the structure of α-lactalbumin and conversion of recombinant protein as described above and native α-lactalbumin to biologicially active complex on an oleic acid-conditioned matrix. (A) shows the structure of α-Lactalbumin containing eight cysteines, which form four disulfide bonds located throughout the protein. The disulfide bonds are shown in black and the residue numbers of cysteines involved are marked. The calcium ion is shown in black. The ribbon structure was obtained from PDB accession number 1HML (10) and modified by MOLMOL (Anderson et al., Biochemistry 1997 36 (39) 11648-11654. (B) This is a graph showing the elution of complex over time at low salt (Fraction 1) and high salt (Fraction 2). To form the complex, recombinant protein of SEQ ID NO 2 was applied to an oleic acid conditioned ion exchange column and the complex was eluted with a NaCl gradient (conductivity trace in light grey). Human α-lactalbumin with EDTA or without EDTA was used as control. (C) This is a table showing conversion yields as determined as the area under the curve from (B) 0-110 min (fraction 1) and 110-140 min (fraction 2).

FIG. 2. shows the results of circular dichroism spectroscopy of α-lactalbumin and various complexes s. (A) The tertiary structure of the recombinant protein having the sequence of α-lactalbumin in which all cysteines have been convered to alanines (black solid line) and the biologically active complex obtained therefrom (designated Cys567OA) (black dashed line) was examined by near-UV CD spectroscopy. The spectra were recorded at 70 μM in 5 mM Tris, pH 8.5 with native α-lactalbumin (grey solid line), apo α-lactalbumin (grey cross) and HAMLET (grey dashed line) as controls. The spectra of human α-lactalbumin, α-lactalbumin$^{All-Ala}$ and HAMLET have been described previously. (B) The secondary structure of HAMLET (grey dashed line) and Cys567OA (black dashed line) was examined with far-UV CD spectroscopy. The recorded spectra of the controls, α-lactalbumin (grey solid line) and α-lactalbumin$^{All-Ala}$ (black solid line), were consistant with previous reports. The spectra were recorded at 28 μM in 5 mM Tris, pH 8.5.

FIG. 3. compares the effect of HAMLET and the biological complex of the present invention in killing tumor cells. (A) L1210, (B) Jurkat, (C) HeLa and (D) A549 cells were exposed to HAMLET or Cys567OA for 6 hours. The lymphoma cells (L1210 and Jurkat) were treated with 7, 14 and 21 μM of HAMLET and the carcinoma cells (A549 and HeLa) with 14, 28 and 42 μM. Cell death was determined by Trypan blue exclusion, in percent of untreated cells, and shown in the left panel. The decrease in ATP levels by HAMLET (black triangle) and Cys567OA (black circle) are shown in the right panel, in percent of the medium control. Averages of two to five experiments are shown with standard deviation as error bars. α-Lactalbumin (grey triangle) and α-lactalbumin$^{All-Ala}$ (grey circle) proteins were used as controls. Cys567OA was shown to be as biologically active as HAMLET, and particularly more active in HeLa and A549 cell lines.

Figure 4:
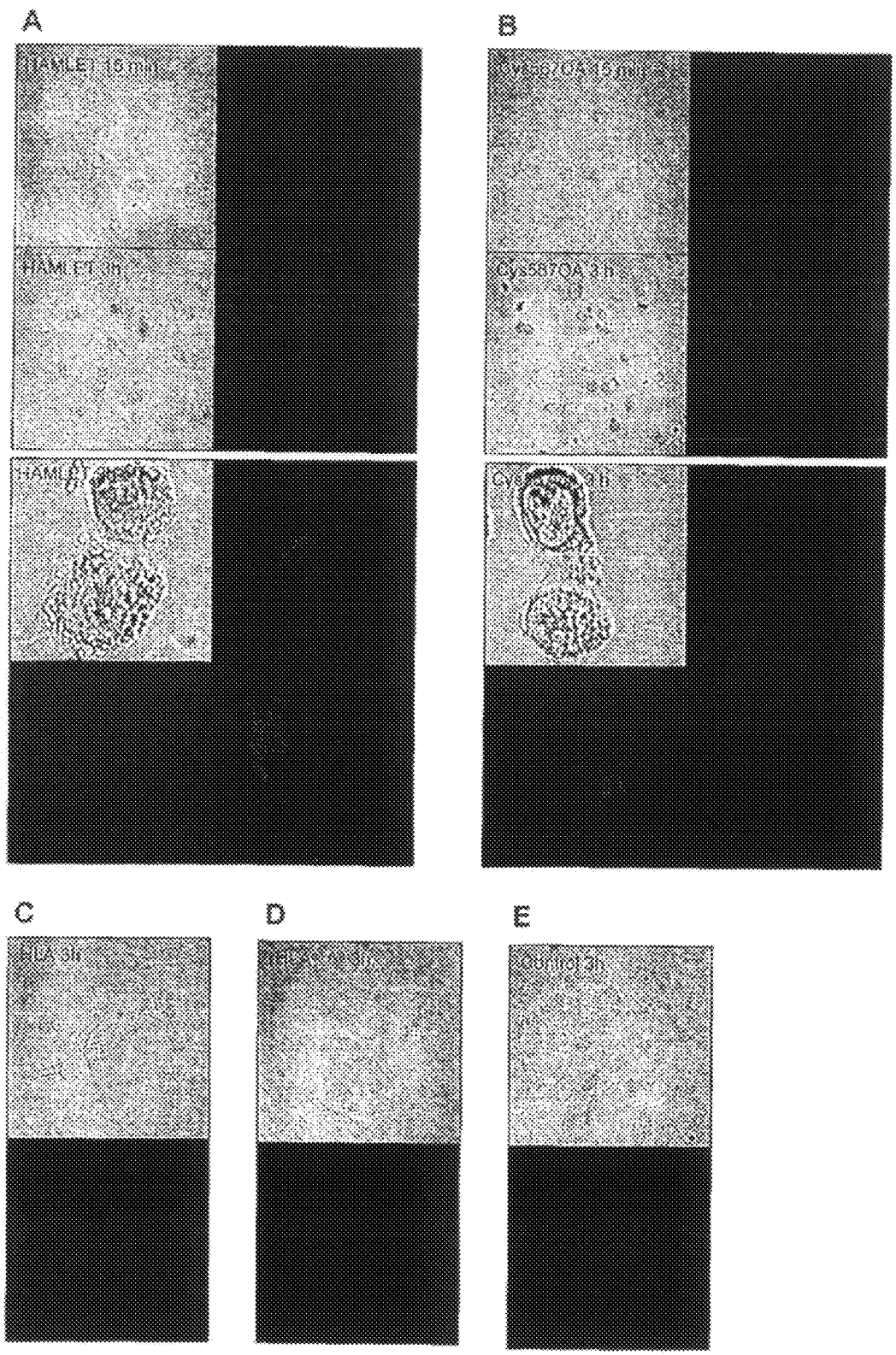

FIG. 4 illustrates cellular internalization of Alexa-labeled complexes. The internalization of the biological complex of the invention (Cys567OA) by A549 cells was examined by confocal microscopy using Alexa-fluor labeled complex. α-Lactalbumin, recombinant protein having the sequence of α-lactalbumin with all cysteines substituted by alanines and HAMLET were used as controls. The cells were treated for 15 min and 3 hours with 35 μM. (A) HAMLET was rapidly internalized by the tumor cells after 15 minutes and after 3 hours a further internalization had occurred. (B) Cys567OA was internalized more slowly than HAMLET, but after 3 hours similar amounts were present in the cells. (C) α-Lactalbumin or (D) α-lactalbumin$^{All-Ala}$ were not internalized by the cells.

Figure 5:
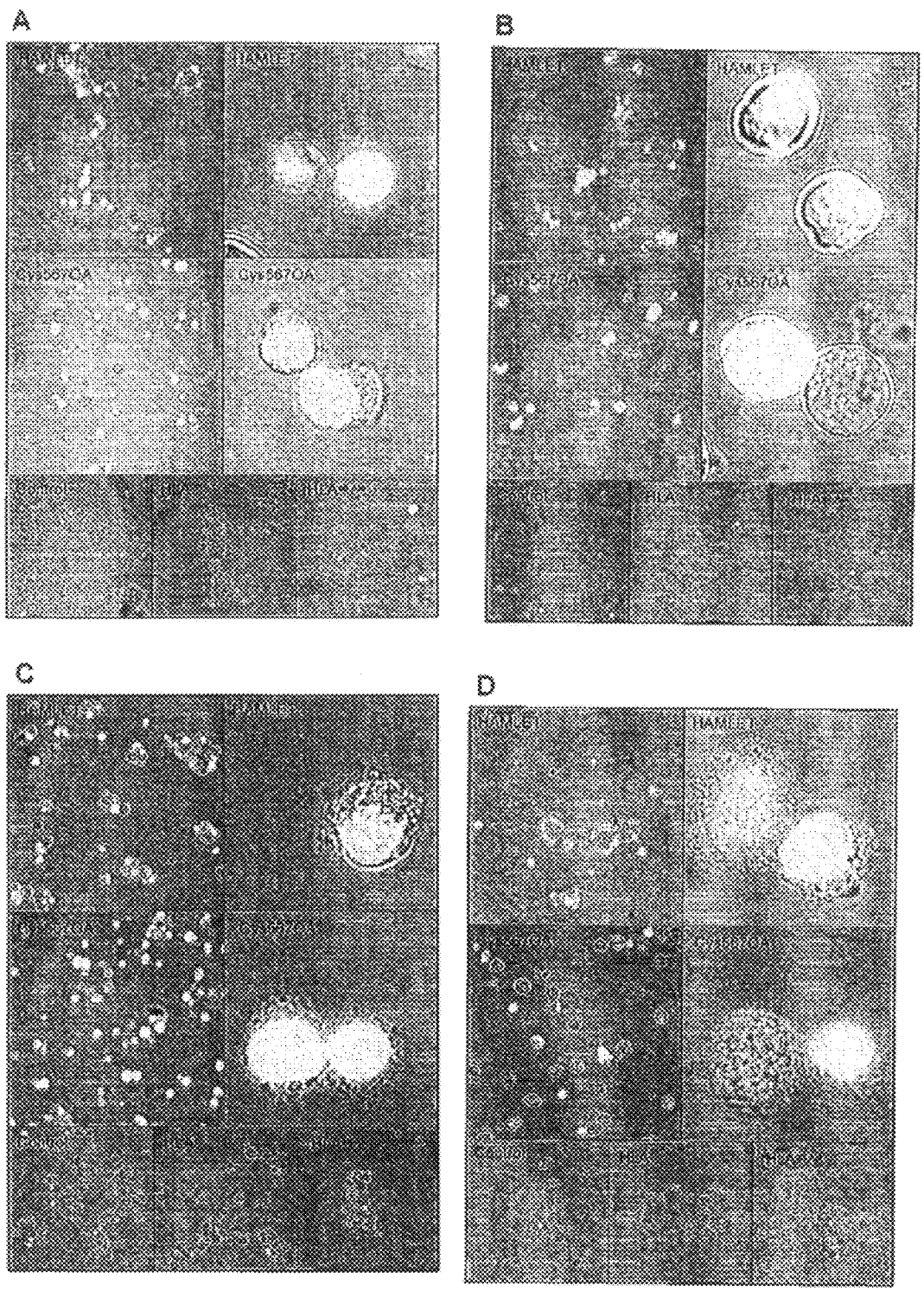

FIG. 5 shows the result of TUNEL staining of human lung carcinoma cells treated with biologically active complexes including the complex of the present invention. Evidence of DNA damage in (A) L1210, (B) Jurkat, (C) HeLa and (D) A549 cells after HAMLET and Cys567OA exposure was examined using TUNEL staining HAMLET and Cys567OA (14 μM in lymphoma cells, 28 μM in carcinoma cells) caused nuclear DNA damage in the four cell lines, indicated by positive TUNEL staining α-Lactalbumin and α-lactalbumin$^{All-Ala}$ (21 μM in lymphoma cells, 42 μM in carcinoma cells) did not cause DNA damage.

Figure 6:
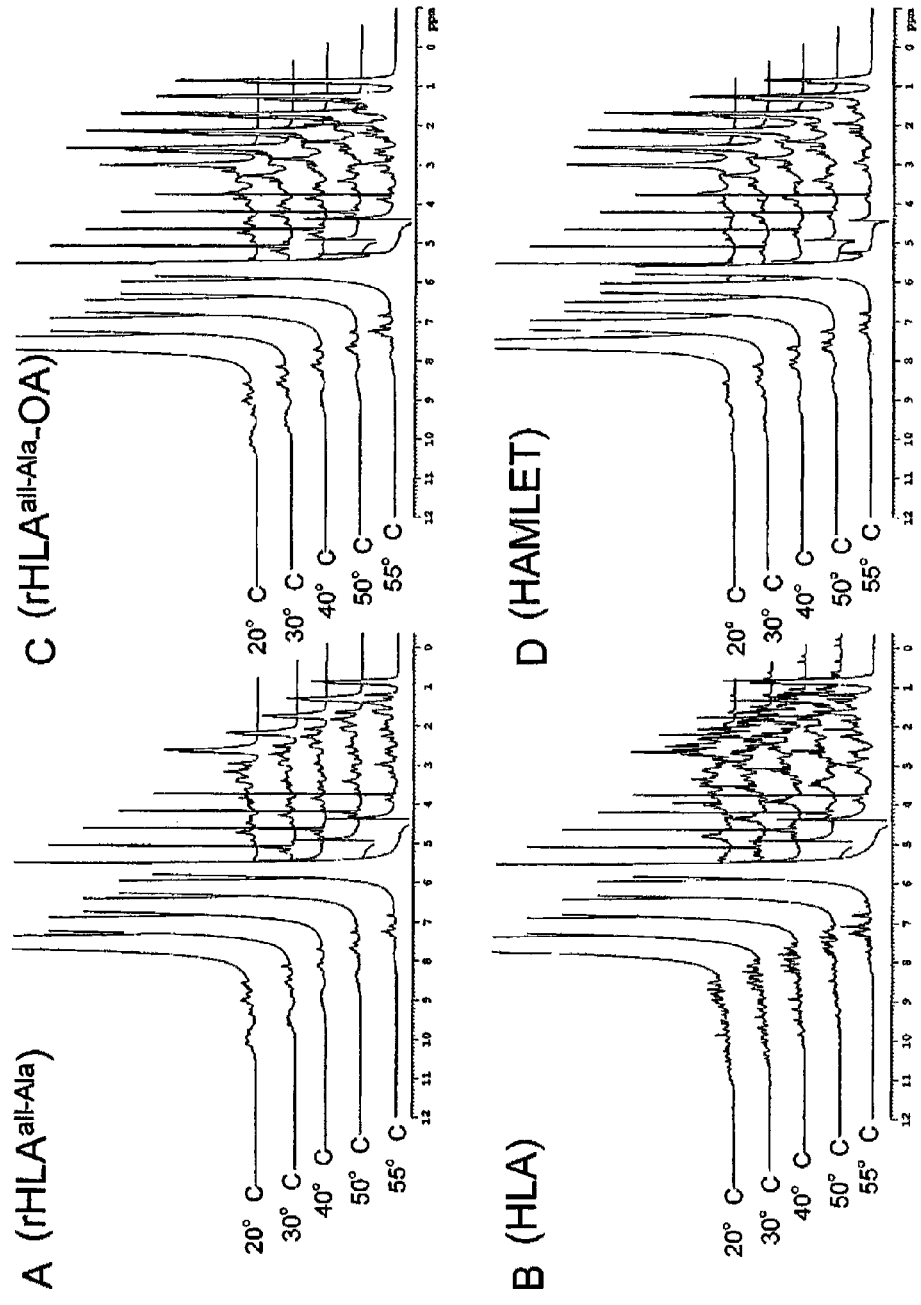
Figure 7:
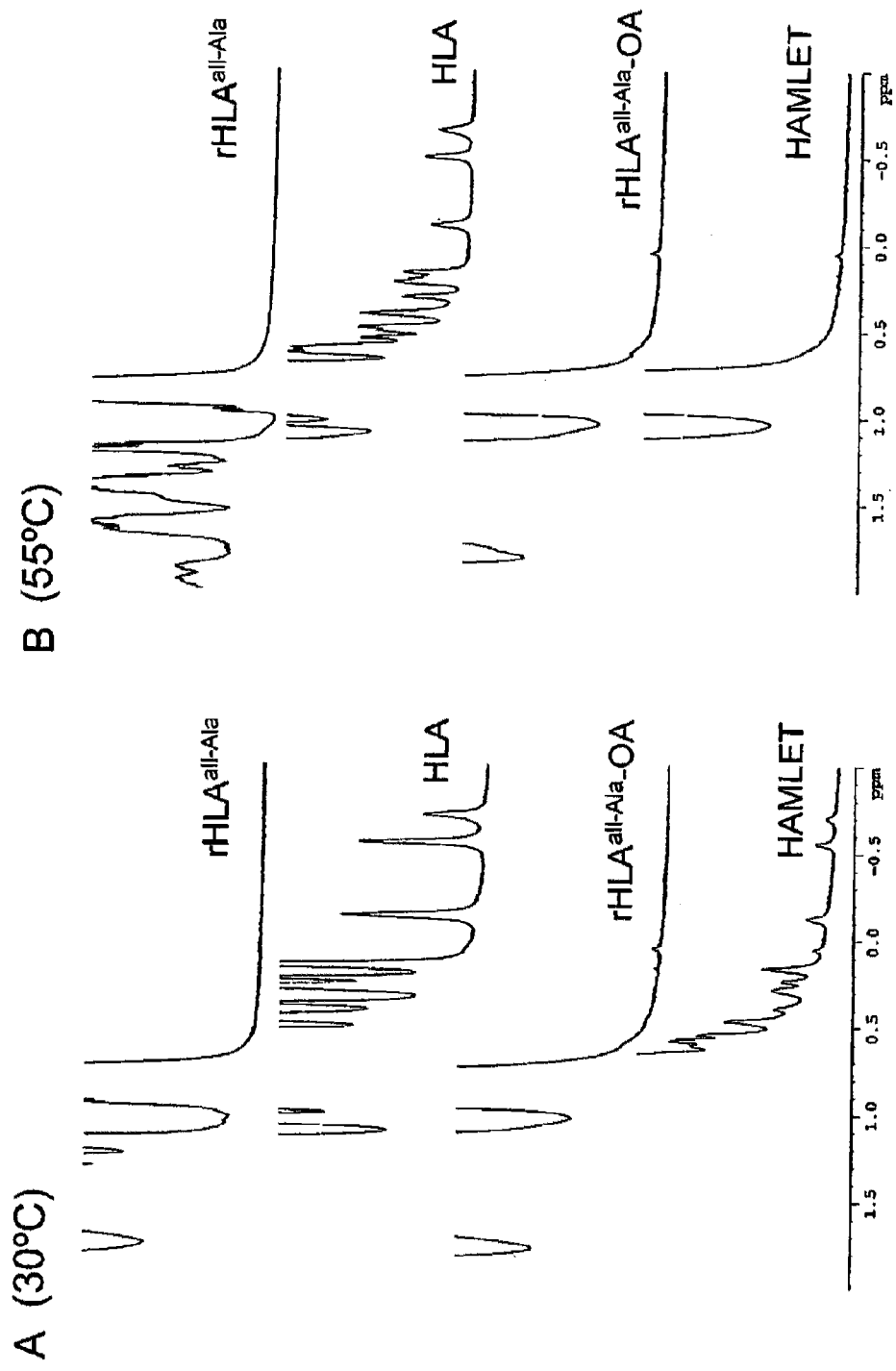

FIGS. 6 and 7 show the results of NMR spectroscopy of human α-lactalbumin (HLA), recombinant human α-lactalbumin as described in below (rHLA$^{all-Ala}$) and protein-oleic acid complexes.

EXAMPLE 1

Protein Expression and Purification

Wild-type α-lactalbumin contains eight cysteines at positions 6, 28, 61, 73, 77, 91, 111 and 120, forming four disulfide bonds, which stabilize the native state (FIG. 1A). Two disulfide bonds are present in the α-domain [6-120, 28-111], one in the β-domain [61-77] and one in the interface between the two domains [73-91]. The protein is also stabilized by a calcium ion, which if removed, makes α-lactalbumin lose its well-defined tertiary structure and adopt a molten globule state.

A vector encoding a recombinant protein having the sequence of human α-lactalbumin in which all cysteines were changed to alanines, pALAALA, obtained by incorporating point mutations in the wildtype vector, pALA, the α-lactalbumin gene cloned into the T7-polymerase-based expression vector pAED4 (HUFF M.E. Curr Opin. Struct. Biol. (2003 13 (6), 674-682) was used. The vector was transformed into *Escherichia coli* BL-21*, the recombinant protein expressed and purified as described previously described (Peng Z. Y. et al., Biochemistry (1995) 34(104), 3241-3252; Schulman B. et al., J. Mol. Biol. 253, 651-657) but with some modifications. Inclusion bodies were solubilized in urea buffer (10 mM Tris, 8 M urea, 5 mM reduced glutathione, pH 8.0) and loaded onto a DEAE-cellulose (Whatman, Brentford, UK) column equilibrated with 20 mM Tris, pH 8.0. The column was washed with 25 mM Tris, 10 mM reduced glutathione, 0.25 M NaCl, pH 8.0 and the protein eluted with 25 mM Tris, 7 M urea, 0.5 M KCl at pH 8.0. Fractions were pooled and dialysed against still tap water for 24 hours and flowing tap water for at least 48 hours (Spectra/Pore, Laguna Hills, Calif., molecular weight cutoff 3.5 kDa). In case of precipitation during dialysis, the precipitate was dissolved in 5 M urea, then dialysed against flowing tap water and lyophilized. The dialyzed sample was loaded onto a DEAE-Sephacel (Amersham Biosciences, Uppsala, Sweden) column equilibrated with 25 mM Tris, 0.2 mM $CaCl_2$ at pH 7.8 then eluted with a linear salt gradient (25 mM Tris, 0.2 mM $CaCl_2$, 0-0.4 M NaCl pH 7.8). Fractions were pooled, dialyzed against distilled water at pH 7 (molecular weight cutoff 3.5 kDa), and lyophilized. The purified mutant protein is of SEQ ID No 2 which is the sequence of human α-lactalbumin but contains an extra N-terminal methionine residue, which was not removed.

The recombinant protein was expressed in *E. coli* BL21* with relatively high yields (100 mg/L culture) and purified to homogeneity. Since, the recombinant protein substitutes all cysteines for alanines, it thereby contains no disulfide bonds. However the native-like topology is known to be preserved. The mutant adopts a molten globule-like conformation, as shown by near-UV CD spectroscopy and by NMR with a retained secondary structure shown by far-UV CD spectroscopy. This protein was designated rHLA$^{all-Ala}$.

EXAMPLE 2

Complex Formation with Oleic Acid by Ion Exchange Chromatography

A column (14 cm×1.6 cm) was packed with 10 ml of DEAE-Trisacryl M (BioSepra, Ville-neuf, France) and conditioned with oleic acid (C18:1:9cis) (Larodan, Malmö, Sweden) as previously described (Svensson et al. Proc. Natl. Acad. Sci. USA (2000) 97(8) 4221-4226 and Pettersson J. et al., Biochem. Biophys. Res. Commun. (2006) 345(1) 260-270). Essentially, ten milligrams of oleic acid was dissolved in 500 μl of 99.5% ethanol by sonication. After addition of 10 mM Tris-HCl ph 8.5 (10 ml), the solution was applied to the column. Five milligrams of protein, (the recombinant protein rHLA$^{all-Ala}$ obtained as described in Example 1), or controls comprising native α-lactalbumin or native α-lactalbumin preincubated with excess EDTA) were dissolved in buffer (50 mM Tris/HCl pH 8.5, 0.1 M NaCl) and added to the column individually.

Fractions were collected after applying a NaCl gradient.

The column was eluted with an NaCl gradient, (Buffer A comprising 10 mM Tris HCL (pH 8.5) followed by Buffer B which was Buffer A containing 1M NaCl) and the fractions eluting before (fraction 1, t=0-110 min) or after high salt (fraction 2, t=110-130 min) were examined (FIG. 1B). The complex obtained using the recombinant protein rHLA$^{all-Ala}$ of Example 1, (Cys567OA) eluted as a sharp peak at the same position as HAMLET. In contrast, wild type α-lactalbumin does not produce any significant complex that eluted after applying high salt (FIG. 1B and C). In fact, the recombinant protein rHLA$^{all-Ala}$ of Example 1 was found to convert to a biologically active complex more efficiently than EDTA-treated α-lactalbumin with a recovery yield of 99% of applied protein (range 87-99%, SD 4.5, n=6) compared to 71% (range 67-94%, SD 11.3, n=5), respectively (FIG. 1C). This may reflect the greater structural homogeneity of the mutant protein's conformation, where a greater proportion of the recombinant protein rHLA$^{all-Ala}$ of Example 1 more readily adopt the molten globule state under the conditions of the chromatographic conversion to the fatty acid-bound complex.

Salt was removed by dialysis against distilled water (Spectra/Pore, membrane cut off 3.5 kDa) followed by lyophilization.

EXAMPLE 3

Circular Dichroism Spectroscopy on the α-Lactalbumin Variants

Far- and near-UV CD spectra were collected on α-lactalbumin, the recombinant protein rHLA$^{all-Ala}$ of Example 1, HAMLET and the Cys567OA obtained using the recombinant protein rHLA$^{all-Ala}$ of Example 1 at 25° C. Lyophilized material was dissolved in 5 mM Tris, pH 8.5 to 70 and 28 μM for near- and far-UV CD spectra, respectively. Near-UV spectra were obtained between 240 and 320 nm and far-UV spectra between 190 and 250 nm. The wavelength step was 1 nm, the response time was 8 sec and scan rate at 10 nm/min.

An average of six scans is presented where the mean residue ellipticity, $\theta_m$ in deg·cm$^2$·dmol$^{-1}$, was calculated as described previously (Svensson M. et al., J. Biol. Chem. (1999) 274 (10), 6388-6396).

Substantial weakening of the tertiary interactions in the recombinant protein rHLA$^{all-Ala}$ of Example 1 was detected by near-UV CD spectroscopy (FIG. 2A), in agreement with the molten globule cases of α-lactalbumin. In fact, at room temperature, apo-α-lactalbumin is not completely molten globular (FIG. 2A), and instead a significant partitioning of the population of protein molecules into native and molten globule states is found, coexisting in equilibrium and resulting in the averaging of spectra. Thus, under identical conditions, a greater proportion of recombinant protein rHLA$^{all-Ala}$ of Example 1 molecules are in the authentic molten globule state, which may contribute to the observed increased conversion yield of the recombinant protein rHLA$^{all-Ala}$ of Example 1 with oleic acid described above. After conversion to a biologically active complex, the near-UV spectrum of the complex was nearly identical to the mutant protein-only spectrum, showing that the binding of oleic acid did not increase the amount of detectable tertiary structure (FIG. 2A).

With regards to secondary structure, the recombinant protein rHLA$^{all-Ala}$ of Example 1 and the biologically active complex obtained therefrom (Cys567OA) both retained a qualitatively similar content of secondary structure with the wild type protein as shown by far-UV CD spectroscopy (FIG. 2B), again correlating well with previous studies.

EXAMPLE 4

Cell death assays

Mouse lymphoma cells (L1210, ATCC, CCL-219), human lymphoma cells (Jurkat, ATCC, TIB-152), human lung carcinoma cells (A549, ATCC, CCL-185) and human cervical carcinoma cells (HeLa, ATCC, CCL-2) were used for examining the tumoricidal activity of Cys567OA. The cells were harvested, washed and resuspended in RPMI 1640 medium (PAA Laboratories GmbH, Pasching, Austria) in the absence of fetal calf serum. For adherent cells, versene (140 mM NaCl, 2.4 mM KCl, 8 mM Na$_2$HPO$_4$, 1.6 mM KH$_2$PO$_4$, 0.5 mM EDTA, pH 7.2) was used for detachment. The cells were seeded into 24 well plates at 1×10$^6$ cells/well (TPP, Trasadingen, Switzerland). The lyophilized material was dissolved at 0.7 mM (MW 14,200 g/mol) in phosphate-buffered saline (PBS) and added to wells to a final concentration between 7 and 42 μM. The stated concentration of HAMLET and Cys567OA refer to the molarities of the protein moiety. Cells were incubated 37° C. in 5% CO$_2$ atmosphere and foetal calf serum was added to each well to a final concentration of 5% after 1 hour. Cell viability was determined after 6 hours using Trypan blue exclusion with interference contrast microscopy (Laborlux 12, Leitz Wetzlar, Germany). ATP levels were determined using ATP Lite (Luminescence ATP detection assay system, PerkinElmer, Boston, Mass.) and luminescence was detected using a luminometer (LUMIstar, BMG Labtech, Offenburg, Germany).

The loss of viability after 6 hours was quantified as the decrease in ATP levels and the increase in Trypan blue staining (FIG. 3). Cys567OA was shown to kill the tumor cells in a dose-dependent manner. More than 80% of all cells were killed after 6 hours of exposure to the highest concentration tested (21 μM for lymphoma cells and 42 μM for carcinoma cells). Similar results were obtained for HAMLET, with more than 60% of the cells killed after 6 hours exposure to the highest concentration. There was no statistically significant difference in tumoricidal activity between the two complexes ($p>0.05$, one-way ANOVA). The results show that the Cys567OA is as active as HAMLET.

In addition, similar to the native protein-only control, the recombinant protein rHLA$^{all-Ala}$ of Example 1 alone did not reduce cell viability (FIG. 3). A statistically significant difference in viability of cells treated with the complex obtained as described above and the fatty acid-free recombinant protein rHLA$^{all-Ala}$ of Example 1 was observed ($p<0.005$, one-way ANOVA). Many studies have suggested that partial unfolding of proteins followed by oligomerization and aggregation result in amyloid structures with cytotoxic properties. In the case of the acidic molten globule form of α-lactalbumin (the "A-state"), amyloid fibrils are indeed known to form in the presence of high concentrations of salt. However, such solution conditions are not used here with the recombinant protein rHLA$^{all\text{-}Ala}$ of Example 1, thereby showing that partial unfolding to the molten globule form alone does not make the protein cytotoxic.

Differences in effect on cell viability were compared using one-way analysis of variance (ANOVA) followed by the Bonferroni Multiple Comparisions test. Analyses were performed using GraphPad InStat3 for Macintosh version 3.0b.

EXAMPLE 5

Uptake of Cys567OA in Tumor Cells

The cellular uptake of the recombinant protein and Cys567OA obtained therefrom was studied using AlexaFluor 568-labeled protein (Molecular Probes, Invitrogen, Carlsbad, Calif.). Human lung carcinoma cells (A549) were seeded onto 8-well chamber slides (Nunc, Rochester, N.Y.) to a density of 50,000 cells per well and incubated overnight at 37° C. in 5% $CO_2$. ALEXA-labeled and unlabeled protein was mixed to a 1:10 ratio and applied to the cells to a final concentration of 35 μM in absence of fetal calf serum. Cells were incubated in 37° C., 5% $CO_2$ and cells were fixated in 3.7% formaldehyde after 15 min. When incubating for 3 h, fetal calf serum was added after one hour to a final concentration of 5%. Cellular uptake was analyzed by confocal microscopy (LSM510 META confocal system, Carl Zeiss, Jena, Germany) and the result shown in FIG. 4. HAMLET—obtained using native α-lactalbumin as described in Example 2 above was used as a control.

As expected, HAMLET was rapidly internalized by the tumor cells, as shown after 15 minutes of exposure (FIG. 4A). After 3 hours a further increase had occurred. Cys567OA showed a similar pattern with rapid internalization followed by a translocation to the nuclei (FIG. 4B). Uptake was weak after 15 minutes when compared with HAMLET, but after 3 hours a similar number of cells had taken up Cys567OA. The reason for the slight difference in uptake kinetics was not immediately obvious, however it is thought that the relatively greater flexibility of the recombinant protein within the Cys567OA complex may bear some responsibility in delaying the initial uptake.

Internalization of the mutant protein without oleic acid was also compared to Cys567OA (35 μM of Cys567OA or of the recombinant protein rHLA$^{all\text{-}Ala}$ of Example 1) (FIGS. 4C and D). The mutant protein bound to the cell surface but was not internalized by the tumor cells. Large aggregates of the recombinant protein were formed and some remained adherent to the cell surface at 15 minute and 3 hours (FIG. 4D).

The results show that internalization into tumor cells is a general feature of HAMLET and Cys567OA, suggesting that the fatty acid cofactor is needed for uptake into tumor cells as well as for the tumoricidal activity. Furthermore, there was no evidence that the recombinant protein itself could be internalized.

EXAMPLE 6

TUNEL Staining

HAMLET has been shown to cause DNA damage in tumor cell lines and in vivo in human tumors using the TUNEL assay (Mossberg et al. Int. J. Cancer (2007) 121(6) 1352-1359). To examine the extent of DNA damage in response to Cys567OA, the four tumor cell lines used in Example 4 were exposed to the complex for 6 hours (14 μM for lymphoma cells and 28 μM for carcinoma cells). HAMLET, recombinant protein rHLA$^{all\text{-}Ala}$ of Example 1 and α-lactalbumin were used as controls.

Cells were harvested by centrifugation and fixed in 4% paraformaldehyde diluted in PBS. The cells were centrifuged onto L-lysine coated microscope slides (25×g, 5 min, Cytospin 3, Shandon, Cheshire, GB) and stored at −20° C. Cells with nuclear DNA damage were identified by the TUNEL assay (Roche, Basel, Switzerland). Briefly, the slides were thawed at room temperature, washed twice in PBS and permeabilized with 0.1% sodium citrate, 0.1% Triton X-100. TUNEL reaction mixture was applied and the slides were incubated at 37° C. in 5% $CO_2$ for 1 h. Slides were washed three times with PBS, mounted with coverslip and mounting medium (Sigma-Aldrich, St Louise, Mo., USA) and examined by confocal microscopy.

Cys567OA caused DNA damage detected by TUNEL staining in all cell types (FIG. 5). The frequency of TUNEL positive cells was similar to that in HAMLET-treated cells. In contrast, the recombinant protein rHLA$^{all\text{-}Ala}$ of Example 1 and α-lactalbumin did not influence TUNEL staining. The results show that the cytotoxic effect of both the oleic acid/molten globule complexes includes damage of nuclear DNA.

In summary, the recombinant protein rHLA$^{all\text{-}Ala}$ of Example 1 having the sequence of α-lactalbumin in which all eight cysteine residues are substituted for alanines, rendering the protein non-native under all conditions is readily converted to a biologically active complex in the presence of oleic acid. In fact, the production process was surprisingly good, giving an enhanced yield in a single peak. This is particularly advantageous in manufacturing terms. Furthermore the complex obtained exhibited strong tumoricidal activity against lymphoma and carcinoma cell lines. By confocal microscopy, it was shown to accumulate within the nuclei of tumor cells, thus reproducing the cellular trafficking pattern of HAMLET with identical tumoricidal activity. Therefore, Cys567OA represents a particularly preferred drug candidate.

EXAMPLE 7

Structural Study of Cys567OA
(Experimental Procedure)

$^1$H NMR spectroscopy—recombinant human α-lactalbumin rHLA$^{all\text{-}Ala}$ as described in Example 1, HAMLET and Cys567OA were solvent-exchanged to sodium phosphate buffer, pH 7.0 with 2.0 M urea using a 2.0 ml Zeba spin desalting column (Thermo Scientific). Human HLA, which contains a bound $Ca^{2+}$ ion, was solvent-exchanged to 2.0 M urea in distilled water, and the pH adjusted to 7. In all cases, the solvents contained 10% $D_2O$. One-dimensional $^1$H NMR spectroscopy of the four samples were acquired on a 600 MHz Ultrashield spectrometer with an indirect detection cryoprobe (Bruker BioSpin). Temperatures of 20° C., 30° C., 40° C., 50° C., and 55° C. were maintained with a variable temperature unit.

Apart from HLA, the one-dimensional $^1$H NMR spectra of the rHLA$^{all\text{-}Ala}$, HAMLET and Cys567OA were poorly resolved and highly broadened as would be found with molten globule species of α-lactalbumin (FIGS. 6A-D). One of the key spectral features of native or native-like three-dimensional structure in α-lactalbumin is the intense upfield-shifted methyl resonances corresponding to the δ$CH_3$ protons of Ile95 (−0.7 ppm at 30° C.) and the γ$CH_3$ protons of Val92 (−0.5 ppm at 30° C.) (FIGS. 6B and 7A). Using this criterion, it was immediately apparent that HAMLET, despite its broad peaks throughout the spectrum in general, still contained considerable native-like structure (FIG. 7A), albeit at a much lower population than folded HLA. This was consistent with the near-UV CD spectrum, where the ellipticity amplitudes of HAMLET was intermediate of apo-HLA and rHLA$^{all-Ala}$/Cys567OA. As a means to further distinguish the samples, each protein or protein-fatty acid complex was subjected to gradually higher temperatures in the presence of 2.0 M urea. The reason for adding urea was two-fold: first to aid in the solubility of the proteins, especially for rHLA$^{all-Ala}$, and second, to subtly increase the dynamic properties of the molecules to distinguish between conformational fluctuations on the microsecond to millisecond timescale (those that are observed in molten globules) from faster timescales (those that are observed with unfolded, highly dynamic molecules). It was noted that the addition of 2M urea did not strip the oleic acid from the proteins, nor does its presence negatively affect the cytotoxic activity of HAMLET and Cys567OA (30 min incubation with 2M urea and phosphate buffered saline; data not shown).

For the case of HLA, starting from a wide dispersion of chemical shifts and well-defined peaks as a result of a fully folded, native structure (20° C. and 30° C.), the peaks gradually broadened while the chemical shift dispersion appeared to narrow in range (40° C. to 55° C.) (FIG. 6B). The characteristic upfield-shifted methyl resonances were still present at high temperature, however the peak heights become increasingly smaller as they broadened (FIG. 7A,B), suggesting that there existed a significant population of molten globule molecules at 55° C. in the presence of 2.0 M urea. For comparison, the conditions for the classical high-temperature molten globule state of α-lactalbumin is approximately 90° C. (pH 7, no chemical denaturant). In contrast, the spectrum of rHLA$^{all-Ala}$ begins with poor chemical shift dispersion and broad peaks (20° C. and 30° C.), but at higher temperatures, even as the chemical shifts narrows further, the peaks gradually sharpen (40° C. to 55° C.) (FIG. 6A). This indicates that the protein is undergoing a transition from the molten globule state to an increasingly loose, unfolded state. One important aspect is that there are absolutely no upfield-shifted methyl resonances at any temperature in this variant (FIG. 7A,B), suggesting that rHLA$^{all-Ala}$ lacks strong inter-residue side-chain interactions at all temperatures, as also suggested by the features found in the near-UV CD spectrum (not shown).

As noted above, the spectra of HAMLET (20° C. and 30° C.; FIG. 7) displayed the δCH$_3$ protons of Ile95 (−0.7 ppm at 30° C.) and the γCH$_3$ protons of Val92 (−0.5 ppm at 30° C.), indicative of a presence of native-like three-dimensional structure albeit at lower populations than HLA. Upon increasing the temperature, as many of the peaks sharpen (FIG. 6D) these upfield resonances vanish (FIG. 7B), suggesting that although partially native-like at lower temperatures, HAMLET's overall behaviour was markedly different from that of native HLA. In fact, the upfield NMR spectrum of HAMLET is found to be identical to that of Cys567OA at 55° C. (FIG. 7B), where there are no upfield resonances except for a very small peak at 0.05 ppm. Surprisingly for Cys567OA, as the temperature is increased and the peaks sharpen as expected of molten globules (FIG. 6C), there is no change in the upfield region (FIG. 7A,B).

In this series of experiments, temperature-varied $^1$H NMR spectroscopy has been exploited to differentiate (i) the spectrally well-dispersed, narrow peak-exhibiting native state, (ii) the spectrally poorly-dispersed, broad peak-exhibiting molten globule states, and (iii) the spectrally poorly-dispersed, narrow peak-exhibiting unfolded states of rHLA$^{all-Ala}$, HLA, HAMLET and Cys567OA. Significant work on the backbone dynamics has been done with greater detail on α-lactalbumin and its varied molten globule states, as well as other archetypal proteins such as apomyoglobin. These bodies of work show the intricacies and nuances of backbone dynamics with regards to different structural regions under different experimental conditions. One of the key conclusions reached from this work is firstly that Cys567OA is clearly structurally different from HAMLET under physiological conditions. Furthermore, whereas HAMLET contains a population of native-like molecules, Cys567OA is completely devoid of native-like side-chain packing, but nevertheless exhibits equivalent cytotoxic activity as HAMLET. Hence, unlike amyloid fibril examples, deliberately engineered, non-native, and partially unfolded structural ensembles can confer independent beneficial effects to the cells depending on the environment.

The invention claimed is:

1. A method for producing a biologically active complex, said method comprising contacting a recombinant α-lactalbumin protein, which lacks intra-molecular disulfide bonds, with oleic acid under conditions in which a biologically active complex is formed, and isolating the biologically active complex, wherein cysteine residues in native α-lactalbumin have been changed to other amino acid residues in the recombinant protein.

2. The method of claim 1 wherein all the cysteine residues have been changed.

3. The method of claim 2 wherein the cysteine residues have been changed to alanine residues.

4. The method of claim 1 wherein the α-lactalbumin is human α-lactalbumin.

5. The method of claim 1 wherein the contacting with the oleic acid occurs on an anion exchange column.

6. The method of claim 5 wherein the column is eluted with a linear salt gradient, and the biologically active complex is isolated from a single fraction eluting at high salt concentration.

7. The method of claim 6 wherein the high salt concentration is 1 M NaCl.

8. The method of claim 1 wherein the recombinant protein comprises SEQ ID NO: 1, optionally with up to 20 amino acids attached at the terminal ends of the protein.

9. The method of claim 8 wherein the recombinant protein is SEQ ID NO: 2.

10. A biologically active complex comprising a recombinant α-lactalbumin protein, which that lacks intra-molecular disulfide bonds, and oleic acid, wherein cysteine residues in native α-lactalbumin have been changed to other amino acid residues in the recombinant protein.

11. The biologically active complex of claim 10 wherein the recombinant protein is SEQ ID NO: 1 or SEQ ID NO: 2.

12. A pharmaceutical composition comprising the biologically active complex of claim 10 in combination with a pharmaceutically acceptable carrier.

13. The biologically active complex of claim 10 for use in inhibiting the growth of cancer cells.

14. A method for increasing the yield of a biologically active complex comprising α-lactalbumin and oleic acid, said method comprising contacting a recombinant α-lactalbumin protein, which lacks at least some intra-molecular disulfide bonds, with oleic acid under ion exchange conditions, wherein cysteine residues in native α-lactalbumin have been changed to other amino acid residues in the recombinant protein.

15. The method of claim 14 wherein all the cysteine residues have been changed.

16. A method for inhibiting the growth of a cancer cell, the method comprising contacting the cancer cell with a biologically active complex comprising a recombinant α-lactalbumin protein, which lacks intra-molecular disulfide bonds, and oleic acid, wherein cysteine residues in native α-lactalbumin have been changed to other amino acid residues in the recombinant protein.

* * * * *

SEQUENCE LISTING

<160> NUMBER OF SEQ ID NOS: 2

<210> SEQ ID NO 1
<211> LENGTH: 123
<212> TYPE: PRT
<213> ORGANISM: Artificial Sequence
<220> FEATURE:
<223> OTHER INFORMATION: SYNTHESIZED

<400> SEQUENCE: 1

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Ala Lys Ser Ser
    50                  55                  60

Gln Val Pro Gln Ser Arg Asn Ile Ala Asp Ile Ser Ala Asp Lys Phe
65                  70                  75                  80

```
Leu Asp Asp Asp Ile Thr Asp Ile Met Ala Ala Lys Lys Ile Leu
            85                  90                  95

Asp Ile Lys Gly Ile Asp Tyr Trp Leu Ala His Lys Ala Leu Ala Thr
            100                 105                 110

Glu Lys Leu Glu Gln Trp Leu Ala Glu Lys Leu
        115                 120

<210> SEQ ID NO 2
<211> LENGTH: 124
<212> TYPE: PRT
<213> ORGANISM: Artificial Sequence
<220> FEATURE:
<223> OTHER INFORMATION: SYNTHESIZED

<400> SEQUENCE: 2

Met Lys Gln Phe Thr Lys Ala Glu Leu Ser Gln Leu Leu Lys Asp Ile
1               5                   10                  15

Asp Gly Tyr Gly Gly Ile Ala Leu Pro Glu Leu Ile Ala Thr Met Phe
            20                  25                  30

His Thr Ser Gly Tyr Asp Thr Gln Ala Ile Val Glu Asn Asn Glu Ser
        35                  40                  45

Thr Glu Tyr Gly Leu Phe Gln Ile Ser Asn Lys Leu Trp Ala Lys Ser
    50                  55                  60

Ser Gln Val Pro Gln Ser Arg Asn Ile Ala Asp Ile Ser Ala Asp Lys
65                  70                  75                  80

Phe Leu Asp Asp Asp Ile Thr Asp Ile Met Ala Ala Lys Lys Ile
                85                  90                  95

Leu Asp Ile Lys Gly Ile Asp Tyr Trp Leu Ala His Lys Ala Leu Ala
            100                 105                 110

Thr Glu Lys Leu Glu Gln Trp Leu Ala Glu Lys Leu
        115                 120
```